US009050390B2

(12) United States Patent
Rizzoli et al.

(10) Patent No.: US 9,050,390 B2
(45) Date of Patent: *Jun. 9, 2015

(54) KNEADABLE AND PLIABLE BONE REPLACEMENT MATERIAL

(71) Applicant: DEPUY SYNTHES PRODUCTS, LLC, Raynham, MA (US)

(72) Inventors: Giancarlo Rizzoli, Bern (CH); Thierry Stoll, Sutz (CH); Reto Luginbuhl, Spiez (CH); Marc Bohner, Aarau (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,458

(22) Filed: Dec. 9, 2013

(65) Prior Publication Data

US 2014/0093571 A1 Apr. 3, 2014

Related U.S. Application Data

(63) Continuation of application No. 10/510,028, filed as application No. PCT/CH03/00216 on Apr. 2, 2003, now Pat. No. 8,603,184.

(30) Foreign Application Priority Data

Apr. 3, 2002 (WO) ..................... PCT/CH02/00184

(51) Int. Cl.
*A61F 2/28* (2006.01)
*A61L 27/10* (2006.01)
*A61L 27/44* (2006.01)
*A61L 27/46* (2006.01)
*A61L 27/52* (2006.01)
*A61L 27/56* (2006.01)
*A61L 27/12* (2006.01)

(52) U.S. Cl.
CPC . *A61L 27/10* (2013.01); *A61F 2/28* (2013.01); *A61F 2310/00293* (2013.01); *A61L 27/446* (2013.01); *A61L 27/46* (2013.01); *A61L 27/52* (2013.01); *A61L 27/56* (2013.01); *A61L 2430/02* (2013.01); *A61L 27/12* (2013.01)

(58) Field of Classification Search
CPC ......... A61L 27/12; A61L 27/10; A61L 27/52; A61F 2310/293
See application file for complete search history.

(56) References Cited

U.S. PATENT DOCUMENTS

| 3,379,541 A | 4/1968 | Tuvell |
| 3,913,229 A | 10/1975 | Driskell |
| 4,046,858 A | 9/1977 | Barsa |
| 4,048,300 A | 9/1977 | Tomlinson |
| 4,097,935 A | 7/1978 | Jarcho |
| 4,113,500 A | 9/1978 | Ebinhara |
| 4,131,597 A | 12/1978 | Bluethgen |
| 4,135,935 A | 1/1979 | Pfeil |
| 4,149,893 A | 4/1979 | Aoki |
| 4,207,306 A | 6/1980 | Jarcho |
| 4,222,128 A | 9/1980 | Tomonaga |
| 4,223,412 A | 9/1980 | Aoyagi |
| 4,224,072 A | 9/1980 | Stewart |
| 4,230,455 A | 10/1980 | Hidaka |
| 4,274,879 A | 6/1981 | Irvine |
| 4,308,064 A | 12/1981 | Takami |
| 4,322,398 A | 3/1982 | Reiner |
| 4,324,772 A | 4/1982 | Conn |
| 4,330,514 A | 5/1982 | Nagai |
| 4,497,075 A | 2/1985 | Niwa |
| 4,596,574 A | 6/1986 | Urist |
| 4,610,692 A | 9/1986 | Eitenmuller |
| 4,623,553 A | 11/1986 | Ries |
| 4,629,464 A | 12/1986 | Takata |
| 4,654,314 A | 3/1987 | Takagi |
| 4,673,355 A | 6/1987 | Farris |
| 4,693,986 A | 9/1987 | Vit |
| 4,699,742 A | 10/1987 | Nakamura |
| 4,713,076 A | 12/1987 | Draenert |
| 4,780,450 A | 10/1988 | Sauk |
| 4,795,467 A | 1/1989 | Piez |
| 4,869,906 A | 9/1989 | Dingeldein |
| 4,888,366 A | 12/1989 | Chu |
| 5,011,495 A | 4/1991 | Hollinger |
| 5,076,869 A | 12/1991 | Bourell |
| 5,125,971 A | 6/1992 | Nonami |
| 5,135,394 A | 8/1992 | Hakamatsuka |

(Continued)

FOREIGN PATENT DOCUMENTS

DE 3925185 5/1990
EP 0003979 10/1981

(Continued)

OTHER PUBLICATIONS

White et al "Biomaterial aspects of Interpore-200 porous hydroxyapatite" Dental Clinics of North America, 1986, 30(1), abstract; retrieved from Eurpor PubMed Central.*
Oberg and Jones, Machinery's Encyclopedia, 1917, vol. IV, pp. 423-424, The Machinery Publishing Company, Ltd.
Du et al., Formation of calcium phosphate/collagen composites through mineralization of collagen matrix, Journal of Biomedical Materials Research 2000, 50(4), 518-527.
Wang et al., Synthesis of nanophase hydroxyapatite/collagen composite, Journal of Materials Science Letters 1995, 14(7), 490-492.
TenHuisen et al., Formation and properties of a synthetic bone composite: Hydroxyapatite-collagen, Journal of Biomedical Materials Research 1995, 29(7), 803-810.

(Continued)

Primary Examiner — H. Sarah Park
(74) Attorney, Agent, or Firm — Wayne C. Jaeschke, Jr.

(57) ABSTRACT

A kneadable and moldable bone-replacement material includes a mixture of calcium-containing ceramic particles and a hydrogel or a substance which can be swelled into a hydrogel. The ceramic particles are of fully synthetic origin and the individual ceramic particles have a structure which is at least partially cohesive and porous. In addition, the majority of the ceramic particles have a non-spheric shape.

19 Claims, No Drawings

(56) References Cited

U.S. PATENT DOCUMENTS

| | | | |
|---|---|---|---|
| 5,258,028 A | | 11/1993 | Ersek |
| 5,273,964 A | | 12/1993 | Lemons |
| 5,290,494 A | * | 3/1994 | Coombes et al. ............... 264/41 |
| 5,338,772 A | | 8/1994 | Bauer |
| 5,344,456 A | | 9/1994 | Nonami |
| 5,356,629 A | | 10/1994 | Sander et al. |
| 5,422,340 A | | 6/1995 | Ammann |
| 5,425,770 A | | 6/1995 | Piez |
| 5,510,418 A | * | 4/1996 | Rhee et al. ................... 525/54.2 |
| 5,639,402 A | | 6/1997 | Barlow |
| 5,650,108 A | * | 7/1997 | Nies et al. ..................... 264/122 |
| 5,977,204 A | | 11/1999 | Boyan et al. |
| 6,030,635 A | | 2/2000 | Gertzman et al. |
| 6,037,519 A | | 3/2000 | Mckay |
| 6,077,989 A | | 6/2000 | Kandel |
| 6,080,801 A | | 6/2000 | Draenert et al. |
| 6,117,456 A | * | 9/2000 | Lee et al. ..................... 424/602 |
| 6,187,047 B1 | | 2/2001 | Kwan |
| 6,210,715 B1 | | 4/2001 | Starling et al. |
| 6,235,225 B1 | | 5/2001 | Okada |
| 6,323,146 B1 | | 11/2001 | Pugh |
| 6,326,018 B1 | | 12/2001 | Gertzman et al. |
| 6,383,190 B1 | | 5/2002 | Preissman |
| 6,383,519 B1 | | 5/2002 | Sapieszko |
| 6,437,018 B1 | | 8/2002 | Gertzman et al. |
| 6,458,375 B1 | | 10/2002 | Gertzman et al. |
| 6,733,582 B1 | | 5/2004 | Bohner et al. |
| 6,949,251 B2 | | 9/2005 | Dalal |
| 6,991,803 B2 | | 1/2006 | Sapieszko |
| 7,578,845 B2 | | 8/2009 | Nies |
| 8,603,184 B2 | * | 12/2013 | Rizzoli et al. ............... 623/23.56 |
| 2001/0053938 A1 | * | 12/2001 | Dorigatti et al. ........... 623/23.51 |
| 2002/0022885 A1 | | 2/2002 | Ochi |
| 2002/0187104 A1 | * | 12/2002 | Li et al. .......................... 424/44 |
| 2002/0192263 A1 | | 12/2002 | Merboth et al. |
| 2002/0197242 A1 | | 12/2002 | Gertzman et al. |
| 2003/0065400 A1 | * | 4/2003 | Beam et al. ................. 623/23.51 |
| 2003/0143283 A1 | | 7/2003 | Tofe |
| 2005/0288795 A1 | | 12/2005 | Bagga |

FOREIGN PATENT DOCUMENTS

| | | |
|---|---|---|
| EP | 0061108 | 9/1982 |
| EP | 0360244 | 3/1990 |
| EP | 0416398 | 3/1991 |
| EP | 0243178 | 6/1991 |
| EP | 0522569 | 1/1993 |
| EP | 0987032 | 3/2000 |
| EP | 1127581 | 8/2001 |
| GB | 2323083 | 9/1998 |
| JP | 1166763 | 6/1989 |
| JP | 13014571 | 12/1989 |
| JP | 03085179 | 4/1991 |
| JP | 04221538 | 8/1992 |
| JP | 04327525 | 11/1992 |
| JP | 05237178 | 9/1993 |
| JP | 07246235 A | 9/1995 |
| JP | 07313586 | 12/1995 |
| JP | 0824347 | 1/1996 |
| JP | 09201330 | 8/1997 |
| JP | 2002331027 | 11/2002 |
| WO | WO 93/20858 | 10/1993 |
| WO | WO 94/15653 | 7/1994 |
| WO | WO 98/38948 | 9/1998 |
| WO | WO 00/45871 | 8/2000 |
| WO | WO 01/13970 | 3/2001 |
| WO | WO 01/32100 A2 | 5/2001 |
| WO | WO 01/66044 | 9/2001 |
| WO | WO 01/66163 | 9/2001 |
| WO | WO 02/070029 | 9/2002 |
| WO | WO 02/083194 | 10/2002 |
| WO | WO 2004/073563 | 9/2004 |
| WO | WO 2004/091435 | 10/2004 |
| WO | WO 2005/074614 | 8/2005 |

OTHER PUBLICATIONS

Rodrigues et al., Characterization of a bovine collagen-hydroxyapatite composite scaffold for bone tissue engineering, Biomaterials 2003, 24(27), 4987-4997.

Zerwekh, et al., Fibrillar collagen-biphasic calcium phosphate composite as a bone graft substitute for spinal fusion, Journal of Orthopaedic Research 1992, 10(4), 562-572.

Bucholz, Nonallograft Osteoconductive Bone Graft Substitutes, Clinical Orthopaedics & Related Research 2002, 395, 44-52.

Brown et al., Neucoll, Inc., Collagraft® Strip: an Osteoinductive Bone Graft Substitute, OTA 1999 Posters, Poster #95.

Walsh et al., Mechanical and histologic evaluation of Collagraft in an ovine lumbar fusion model, Clin. Orthop. Relat. Res Jun. 2000; (375) 258-66.

Harner, Letter to the Editor, Clin, Orthop. Relat. Res. Jun. 1997; (339) 285.

Muschler et al., Evaluation of Collagen Ceramic Composite Graft Materials in a Spinal Fusion Model, Clinical Orthopaedics and Related Research, 1996, 328, 250-260.

Tay et al., Use of a Collagen-Hydroxyapatite Matrix in Spinal Fusion: A Rabbit Model 1998, 23(21), 2276-2281.

Jahng, et al., Endoscopic instrumented posterolateral lumbar fusion with Healos and recombinant human growth/differentiation factor-5, Neurosurgery, Jan. 2004 54(1), 171-80; discussion 180-1.

"Bulk Density" from Intertek Plastics Technology Laboratories, p. 1, retrieved online on Oct. 6, 2011 (http://www.ptli.com/testlopedia/tests/bulkdensity-d1895.asp).

Chen et al., Polysaccharide hydrogels for protein drug delivery, Carbohydrate Polymers, 28, (1995) 69-76.

Canadian Application Serial No. 2,481,383, Office action mailed Oct. 1, 2009, 3 pgs.

European Patent Application No. 04750971.6, Communication mailed Jun. 12, 2008, 5 pgs.

International Application Serial No. PCT/CH03/00216, International Preliminary Examination Report dated Jul. 1, 2014, (w/English Translation), 12 pgs.

International Application Serial No. PCT/CH03/00216, International Search Report mailed Jun. 11, 2003, (w/English Translation), 8 pgs.

Japanese Application No. 2002-506661, Official Notice of the Reason for the Final Rejection mailed Jul. 11, 2008, (w/English Translation), 4 pgs.

Japanese Application No. 2002-506661, Notice of the Reason for the Rejection mailed Feb. 27, 2008, (w/English Translation), 7 pgs.

Kaneko et al., Synthesis and Swelling—deswelling kinetics of poly(N-isopropylacryamide) hydrogels grafted with LCST modulated polymers, Journal of Biomaterials Science, Polymer Edition, 10 (11), (1999), 1079-1091.

Stile et al., Synthesis and Characterization of Injectable Poly(N-isopropylacrylamide)-Based Hydrogels that Supports Tissue Formation in Vitro, Macromolecules, 32, (1999), 7370-7379.

* cited by examiner

KNEADABLE AND PLIABLE BONE REPLACEMENT MATERIAL

CROSS REFERENCE TO RELATED APPLICATIONS

This application is a continuation of U.S. patent application Ser. No. 10/510,028 filed Dec. 14, 2004, which is the National Stage of International Application No. PCT/CH03/00216 filed Apr. 2, 2003, which claims benefit of Switzerland Patent Application No. PCT/CH02/00184 filed Apr. 3, 2002, the disclosures of which are hereby incorporated by reference as if set forth in their entirety herein.

FIELD OF THE DISCLOSURE

The invention concerns a kneadable and moldable bone-replacement material in accordance with the general term of patent claim 1.

BACKGROUND

Under current standards of technology it is common practice to use blocks or granulates made from synthetically produced calcium phosphate for re-filling of defective bones. The disadvantages of this material lie in the fact that the blocks must be tailored to the shape of the defective bone they are to be used on as well as in the fact that the time spent in the application of the loose granulates is not at optimum level.

In addition, materials which can be injected are also known. These however consist mainly of spheric particles (small balls). These materials with spheric balls can be injected more easily into the bone because the small balls slide past each other with greater ease. This however is a disadvantage in the case of kneadable and moldable bone-replacement materials, as they are meant to be kneaded rather than injected. Such a material should therefore be cohesive, a requirement which is not met by spheric particles.

In the following text, the term "particle" includes any three-dimensional body, regardless of its dimensions, especially the small parts commonly known as "granulate" or "grains".

This discussion regarding current standards of technology is used only to explain the environment of the invention and does not mean that the standards of technology quoted here were actually published or publicly known at the time of this registration or its priority.

SUMMARY

This invention is meant to provide a remedy for this situation. The invention is based on the problem of creating a kneadable bone-replacement material which overcomes the disadvantages listed above, especially the shaping and the time required for application.

The invention solves this task through a kneadable and moldable bone-replacement material which has the characteristics of claim 1.

The advantage of eliminating the danger of transferring diseases due to the absence of possible pathogenic agents such as proteins, germs, viruses or bacteria as compared to bone-replacement materials of natural origin is thus achievable.

Another advantage lies in the fact that it is no longer necessary to transfer the loose ceramic particles laboriously one by one to the desired location of use. Instead, using the kneadable bone-replacement material, the required total quantity of ceramic particles can be transferred to the location of use quickly and easily. In addition, non-spheric and especially angular particles encourage ceramic resorption and accelerate tissue growth and bone recovery. Compared to materials with nearly spheric particles, the non-spheric and especially the angular particles improve the cohesion of the kneadable material.

DETAILED DESCRIPTION

"Non-spheric" describes any particle shape which is significantly different from a spheric shape. One variant of the invention uses ceramic particles with an angular shape. "Angular" describes those particles which have individual edges, especially those which are visible with the naked eye, i.e. which are at least 0.1 mm in size.

Compared to round particles, this results in an increase to the particle surface, while the average particle diameter remains the same. This causes the adhesive interaction between the particles and the hydrogel to be increased, guaranteeing the moldability of the bone-replacement material without the need for increasing the quantity of hydrogel used or its concentration.

There is also a special variant whose ceramic particles have a spheric relationship $S=D_{max}/D_{min}$ between the largest diameter $D_{max}$ and the smallest diameter $D_{min}$ of the individual particles, which is larger than 1.2 and preferably larger than 1.5. The value of S should be larger than 3 and preferably larger than 5.

At least 60% and typically at least 80% of the ceramic particles should be of a non-spheric shape.

The pore size of the ceramic particles should be between 1 and 500 micrometers. The ceramic particles typically have a share of macropores which are between 100 and 500 micrometers in size and a share of micropores which are between 1 and 100 micrometers in size. This guarantees optimum pore size distribution and the growth of autogenous tissue through the pores. The porosity of the ceramic particles should be between 60 and 90 percent. This ensures that autogenous tissue is able to grow through a larger volume share of ceramic particles.

The bulk density of the ceramic particles should between 0.2 g/ccm and 2.0 g/ccm. It is typically between 0.6 g/ccm and 1.0 g/ccm and preferably between 0.7 g/ccm and 0.9 g/ccm. In one variant, the bulk density of the ceramic particles is between 1.0 g/ccm and 2.0 g/ccm, preferably between 0.2 g/ccm and 1.8 g/ccm.

The advantage of the higher bulk density ranges is a higher mechanical stability, the disadvantages however are slower resorption and slower bone re-growth. The advantages of lower bulk density ranges are faster resorption and improved bone re-growth.

The jarring density of the ceramic particles should be between 0.5 g/ccm and 2.5 g/ccm, preferably between 0.7 g/ccm and 1.1 g/ccm or between 1.1 g/ccm and 2.5 g/ccm.

The apparent density of the ceramic particles can be further increased by using ceramic particles of different grain sizes. The interstitial space (dead volume) between the larger particles is filled by smaller particles. The intercaling of the ceramic particles further improves the mechanical characteristics of the kneading material.

The average diameter of the ceramic particles should be between 100 and 250 micrometers. The advantage of this is the fact that the bone-replacement material is compact. In addition, the risk of irritation within the tissue surrounding the particles is practically non-existent, if the diameter of the particles is not smaller than 100 micrometers.

The average diameter of the ceramic particles can also be between 150 and 500 micrometers or between 0.5 and 5.6 mm for more efficient filling of medium-sized and larger defects.

It is also possible to mix ceramic particles with an average diameter between 100 and 250 micrometers and particles with an average diameter between 250 and 500 micrometers or an average diameter between 0.5 and 5.6 mm. This has the advantage that it guarantees the compactness of the bone-replacement material. The interstitial pore volume (pore dead volume) which results from the use of large-grain material can thus be reduced to a minimum. It is also possible to affect the degradation period of the hardened bone-replacement material through the use of ceramic particles of various sizes.

The ceramic particles should consist of a calcium-phosphate, typically beta-tricalcium-phosphate. This means that a ceramic is being used whose stoichiometric makeup is very close to that of the human bone. In addition, the degradation period of beta-tricalcium-phosphate is neither too fast nor too slow, preventing the development of hollow spaces or implanter residue during degradation.

The ceramic particles consisting of calcium-phosphate have the advantage of possessing a molar Ca/P relationship in the range between 1.0 and 2.0 and preferably in the range between 1.45 and 1.52. The range between 1.45 and 1.49 is preferred.

The calcium-phosphate can be selected from the following group: Dicalcium-phosphate-dihydrate ($CaHPO_4 \times 2H_2O$), dicalcium-phosphate ($CaHPO_4$), alpha-tricalcium-phosphate (alpha-$Ca_3(PO_4)_2$), beta-tricalcium-phosphate (beta-$Ca_3(PO_4)_2$), calcium-deficient hydroxylapatite ($Ca_9(PO_4)_5(HPO_4)OH$), hydroxylapatite ($Ca_{10}(PO_4)_6(OH)_2$), carbonated apatite ($Ca_{10}(PO_4)_3(CO_3)_3(OH)_2$), flouride-apatite ($Ca_{10}(PO_4)_6(F,OH)_2$), chloride-apatite ($Ca_{10}(PO_4)_6(Cl,OH)_2$), whitlockite (($Ca,Mg)_3(PO_4)_2$), tetracalcium-phosphate ($Ca_4(PO_4)_2O$), oxyapatite ($Ca_{10}(PO_4)_6O$), beta-calcium-pyrophosphate (beta-$Ca_2(P_2O_7)$), alpha-calcium-pyrophosphate, gamma-calcium-pyrophosphate, octo-calcium-phosphate ($Ca8H_2(PO_4)_6 \times 5H_2O$).

The ceramic particles may also consist of a mixture of different calcium-phosphates. The advantage of such a mixture lies in the control of the resorption period. Due to the differing resorption behaviours of the mixture components, faster bone growth into the cavities of components with faster resorption times can be facilitated.

The ceramic particles can also consist of calcium-sulfate or calcium-carbonate.

For a special variant, the ceramic particles can be selected from the following group: alpha-calcium-sulfate-hemihydrate, beta-calcium-sulfate-hemihydrate, calcium-sulfate-dihydrate.

For another variant, the ceramic particles may consist of a mixture of different calcium-phosphates, calcium-sulfates and/or calcium-carbonates. The advantage of such a mixture lies in the control of the resorption period. Due to the differing resorption behaviours of the mixture components, faster bone growth into the cavities of components with faster resorption times can be facilitated.

The non-spheric particles can be generated by breaking or grinding of larger porous blocks of the desired material. The desired particle sizes can be achieved by using appropriate sieves.

For a special variant, the bone-replacement material may also contain metallic or semi-metallic ion shares. The advantages of such ion contents are their impact upon the resorption behaviour of the ceramic, allowing optimum replacement of the mineral composition of the bone.

The matrix which the hydrogel consists of or the substance which may be swelled into a hydrogel may be selected from the following substance groups:
  a) fully synthetic substances;
  b) natural biological substances of plant origin; and/or
  c) biotechnologically generated substances.

The hydrogel or the substance which can be swelled into a hydrogel can also consist of a mixture of fully synthetic, natural biological or biotechnologically generated substances.

A hydrogel is present when a solid substance is hydrated via a liquid phase, changing and increasing the viscosity of the liquid phase, i.e. jellying or coagulating the liquid phase.

The hydrogel matrix can consist of oligomeric or polymeric shares or of a combination of the two. Pharmaco-additives may be mixed into the bone-replacement material as required. The jellying liquid for the hydrogel can be water, especially deionised water and/or an organic, body-compatible solvent.

For a special variant, the hydrogel or the substance which can be swelled into a hydrogel contains one of the following components: a) polyamino-acids or their derivatives, preferably polylysin or gelatin; b) polysaccharides and their derivatives, preferably glycosaminoglycane or alginate; c) polylipides, fatty acids and their derivatives; d) nucleotides and their derivatives; or a combination of the components as listed in a) through d).

For another variant, the hydrogel or the substance which can be swelled into a hydrogel contains one of the following synthetic components: a) polymethylenoxide or its derivatives; b) polyethylene, polyethylenoxide or their derivatives; c) polypropylene, polypropylenoxide or their derivatives; d) polyacrylate or its derivatives; or a combination of the components as listed in a) through d).

For a special variant, the hydrogel or the substance which can be swelled into a hydrogel is either a glycosaminoglycane or a proteoglycane or a mixture of those two substances. The glycosaminoglycane can be a hyaluron-acid, chondroitinsulfate, dermatansulfate, heparansulfate, heparine or keratansulfate.

The concentration of the ready-to-use, hydrated hydrogel or the ready-to-use, hydrated substance which can be swelled into a hydrogel should be between 0.1% and 20.0%.

The molecular weight of the hydrogel or the substance which can be swelled into a hydrogel should exceed 300,000 Dalton and is preferred to be above 500,000 Dalton. For another variant, the molecular weight of the hydrogel or the substance which can be swelled into a hydrogel exceeds 1,000,000 Dalton and is preferred to be above 1,500,000 Dalton. A larger molecular weight means that a smaller amount of hydrogel is required to achieve a certain level of viscosity. Therefore a large number of viscous jellies can be created with a relatively small hydrogen content.

For a special variant, the hydrogel is a liquid solution of a hyaluronate. The hyaluron-acid consists of glucoron-acid and acetylglucosamine which create the disaccharide hyaluron-acid. The hyaluron-acid has a fibrous, non-branced molecular structure and therefore results in highly viscous liquid solutions.

The liquid solution of the hydrogel typically contains less than 99% water and preferably less than 98% water. In special cases, the liquid solution may contain less than 96.5% water and preferably less than 95% water. Such concentrations have the advantage of guaranteeing the excellent moldability of the bone-replacement material.

The molecular weight of the hyaluron-acid used should be larger than $1.5 \times 10^6$ Dalton. For a special variant, the molecular weight of the hyaluron-acid used is between $0.5 \times 10$ and $1.0 \times 10^6$ Dalton.

For another variant, the molecular weight of the hyaluron-acid used is smaller than $1 \times 10^6$ Dalton and preferably smaller than $0.5 \times 10^6$ Dalton.

For a special variant, the specific gravity of the calcium-containing, porous ceramic particles is between 0.5 and 1.0 g/ccm.

For another variant, the weight relationship A/B between the hydrated hydrogel and the calcium-containing ceramic particles is larger than 0.2 and preferably between 0.2 and 0.5.

For other variants, the weight relationship A/B is between 0.5 and 0.9 or between 0.9 and 1.3 or between 1.3 and 2.0 or between 2 and 5 or larger than 5.

The advantages of these different ranges for the weight relationship of A/B lie in the different kneadabilities and resorption periods. A high content of substance A makes the material more kneadable, but increases resorption; a high level of substance B makes the material less kneadable, but reduces the rate of resorption.

The invention and further developments of the invention are explained in more detail in the following application examples.

Example 1

1.2 g of porous and angular granulate of beta-tricalcium-phosphate (β-TCP) with an approximate size of 500 micrometers and a sphericity degree of S=3.1 were mixed with 2.0 g of a 5% liquid solution of biotechnologically generated natrium-hyaluronate with a molecular weight of 500 kD. The resulting kneadable material was highly suitable as a plastic bone-replacement material. It can be kneaded by hand as desired, molded into the desired shape and placed directly into the bone defect to be filled. The moldability allows optimum filling of bone defects.

Example 2

A mixture of 0.6 g of porous and angular granulates of beta-tricalcium-phosphate (β-TCP) with an approximate size of 100 micrometers and a sphericity degree of S=2.9 and 0.6 g of porous and angular granulates of beta-tricalcium-phosphate (β-TCP) with an approximate size of 500 micron and a sphericity of S=2.7 was mixed with 2.0 g of a 5% liquid solution of biotechnologically generated natrium-hyaluronate with a molecular weight of 900 kD. The resulting kneadable material was highly suitable as a plastic bone-replacement material.

Example 3

A mixture of 0.3 g of porous and angular granulates of beta-tricalcium-phosphate (β-TCP) with an approximate size of 100 micrometers and a sphericity degree of S=2.4 and 0.3 g of porous and angular granulates of beta-tricalcium-phosphate (β-TCP) with an approximate size of 500 micron and a sphericity of S=2.3 was mixed with 1.0 g of a 10% liquid solution of biotechnologically generated natrium-hyaluronate with a molecular weight of 900 kD. The resulting kneadable material was highly suitable as a plastic bone-replacement material.

Example 4

A mixture of 0.3 g of porous and angular granulates of beta-tricalcium-phosphate (β-TCP) with an approximate size of 100 micrometers and a sphericity degree of S=1.8 and 0.3 g of porous and angular granulates of beta-tricalcium-phosphate (β-TCP) with an approximate size of 500 micron and a sphericity of S=2.7 was mixed with 50 mg of biotechnologically generated natrium-hyaluronate with a molecular weight of 900 kD. Then 0.9 g of deionised water were added and thoroughly mixed for 10 minutes. The resulting kneadable material was highly suitable as a plastic bone-replacement material.

Example 5

A mixture of 1.65 g of porous and angular granulates of beta-tricalcium-phosphate (β-TCP) with a grain size of 500 to 700 micrometers and a sphericity degree of S=2.5 and 1.65 g of porous and angular granulates of beta-tricalcium-phosphate (β-TCP) with a grain size of 125 to 500 micrometers and a sphericity of S=2.9 was mixed with 3.0 g of a sterile, liquid 6% solution of natrium-hyaluronate (molecular weight of the natrium-hyaluronate=900 kD) under sterile conditions using a spatula. After 30 minutes, the material was placed into a sterile, tube-shaped container. This sterile kneadable material was highly suitable as a plastic bone-replacement material.

Example 6

A mixture of 1.5 g of porous and angular granulates of beta-tricalcium-phosphate (β-TCP) with a grain size of 500 to 700 micrometers and a sphericity degree of S=2.5 and 2.5 g of porous and angular granulates of beta-tricalcium-phosphate (β-TCP) with a grain size of 125 to 500 micrometers and a sphericity of S=2.9 was mixed with 3.0 g of a sterile, liquid 8% chitosane solution under sterile conditions using a spatula. After 30 minutes, the material was placed into a sterile, syringe-like container. The resulting sterile kneadable material was highly suitable as a plastic bone-replacement material.

Example 7

A mixture of 1.5 g of porous and angular granulates of beta-tricalcium-phosphate (β-TCP) with a grain size of 500 to 700 micrometers and a sphericity degree of S=2.5 and 1.5 g of porous and angular granulates of beta-tricalcium-phosphate (β-TCP) with a grain size of 125 to 500 micrometers and a sphericity of S=2.9 was mixed with 3.0 g of a sterile, liquid 5% solution of rhCollagen under sterile conditions using a spatula. The resulting sterile kneadable material was highly suitable as a plastic bone-replacement material.

Example 8

A mixture of 1.5 g of porous and angular granulates of beta-tricalcium-phosphate (β-TCP) with a grain size of 500 to 700 micrometers and a sphericity degree of S=2.5 and 1.5 g of porous and angular granulates of beta-tricalcium-phosphate (β-TCP) with a grain size of 125 to 500 micrometers and a sphericity of S=2.9 was mixed with 2.5 g of a liquid 5% solution of natrium-alginate. The resulting kneadable material was highly suitable as a plastic bone-replacement material.

Example 9

3.0 g of porous and angular granulates of beta-tricalcium-phosphate (β-TCP) with a grain size of 125 to 500 micrometers and a sphericity degree of S=2.9 were mixed with 2.5 g of a liquid 6.5% polyethylenglycol solution (MG=35 kD) using a spatula. The resulting kneadable material was highly suitable as a plastic bone-replacement material.

Example 10

3.0 g of porous and angular granulates of beta-tricalcium-phosphate (β-TCP) with a grain size of 125 to 500 micrometers and a sphericity degree of S=2.9 were mixed with 2.0 g of a liquid 4% polyethylenoxide solution (MG=511 kD) using a spatula. The resulting kneadable material was highly suitable as a plastic bone-replacement material.

Example 11

3.0 g of porous and angular granulates of beta-tricalcium-phosphate (β-TCP) with a grain size of 125 to 500 micrometers and a sphericity degree of S=2.5 were mixed with 2.2 g of a liquid 10% solution of hydroxymethyl-cellulose using a spatula. The resulting kneadable material was highly suitable as a plastic bone-replacement material.

Example 12

A mixture of 1.5 g of porous and angular granulates of beta-tricalcium-phosphate (β-TCP) with a grain size of 500 to 700 micrometers and a sphericity degree of S=2.5 and 1.5 g of porous and angular granulates of beta-tricalcium-phosphate (β-TCP) with a grain size of 125 to 500 micrometers and a sphericity of S=2.9 was mixed with 2.5 g of a liquid 7% solution of Ploronic 407. Ploronic 407 is a substance with a chemical makeup of $HO(C_2H_4O)_a(C_3H_6O)_b(C_2H_4O)_aH$ with a=101 and b=56. The resulting sterile kneadable material was highly suitable as a plastic bone-replacement material.

Example 13

A mixture of 1.5 g of porous and angular granulates of beta-tricalcium-phosphate (β-TCP) with a grain size of 500 to 700 micrometers and a sphericity degree of S=2.5 and 1.5 g of porous and angular granulates of beta-tricalcium-phosphate (β-TCP) with a grain size of 125 to 500 micrometers and a sphericity of S=2.9 was mixed with 2.5 g of a liquid solution consisting of 0.18 g of natrium-hyaluronate (MG=1.4 million Dalton) and 0.09 g of polyethylenoxide (MG=511 kD). The resulting sterile kneadable material was highly suitable as a plastic bone-replacement material.

Example 14

0.2 g of natrium-malginate (MG=50-500 kD) and 1.0 of porous and angular granulates of beta-tricalcium-phosphate (β-TCP) with a grain size of 500 to 700 micrometers and a sphericity degree of S=2.5 and 1.5 g of porous and angular granulates of beta-tricalcium-phosphate (β-TCP) with a grain size of 125 to 500 micrometers and a sphericity of S=2.9 were mixed thoroughly when dry. 2.0 g of deposited water were then stirred into this mixture. This resulted in a kneadable material which was able to be used as a plastic bone-replacement material.

Example 15

0.18 g of natrium-hyaluronate (MG=1.1-1.3 million Dalton) and 1.0 of porous and angular granulates of beta-tricalcium-phosphate (β-TCP) with a grain size of 500 to 700 micrometers and a sphericity degree of S=2.9 and 1.5 g of porous and angular granulates of beta-tricalcium-phosphate (β-TCP) with a grain size of 125 to 500 micrometers and a sphericity of S=2.5 were mixed thoroughly when dry. 0.5 ml of platelet-rich plasma and 1.5 ml of sterile deionised water were then stirred into this mixture. After thorough mixing, this resulted in an excellent plastic kneadable material which was able to be used as a plastic bone-replacement material.

Example 16

0.18 g of natrium-hyaluronate (MG=1.1-1.3 million Dalton) and 1.0 of porous and angular granulates of beta-tricalcium-phosphate (β-TCP) with a grain size of 500 to 700 micrometers and a sphericity degree of S=2.9 and 1.5 g of porous and angular granulates of beta-tricalcium-phosphate (β-TCP) with a grain size of 125 to 500 micrometers and a sphericity of S=2.5 were mixed thoroughly when dry. 2 ml of fresh blood were then stirred into this mixture. After thorough mixing, this resulted in an excellent plastic kneadable material which was able to be used as a plastic bone-replacement material.

Example 17

A mixture of 0.6 g of porous and angular granulates of dicalcium-phosphate-dihydrate ($CaHPO_4 \times 2H_2O$) with an approximate size of 100 micrometers and a sphericity degree of S=2.9 and 0.6 g of porous and angular granulates of beta-tricalcium-phosphate (β-TCP) with an approximate grain size of 500 micrometers and a sphericity of S=2.7 was mixed with 2.0 g of a 5% liquid solution of biotechnologically generated natrium hyaluronate with a molecular weight of 900 kD. The resulting kneadable material was highly suitable as a plastic bone-replacement material.

Example 18

A mixture of 0.6 g of porous and angular granulates of dicalcium-phosphate (CaHPO4) with an approximate size of 100 micrometers and a sphericity of S=1.5 and 0.6 g of porous and angular granulates of dicalcium-phosphate ($CaHPO_4$) with an approximate size of 500 micrometers and a sphericity of S=2.7 was mixed with 2.0 g of a 5% liquid solution of biotechnologically generated natrium hyaluronate with a molecular weight of 900 kD. The resulting kneadable material was highly suitable as a plastic bone-replacement material.

Example 19

A mixture of 0.3 g of porous and angular granulates of calcium-deficient hydroxylapatite (CDHA; $Ca_9(PO_4)_5(HPO_4)OH$) with a specific surface of 55 sqm/g, an approximate size of 125 micrometers and a sphericity degree of S=1.8 and 0.3 g of porous and angular granulates of calcium-deficient hydroxylapatite (CDHA; $Ca_9(PO_4)_5(HPO_4)OH$) with a specific surface of 55 sqm/g, an approximate size of 500 micrometers and a sphericity of S=2.3 was mixed with 2.7 g of a 10% liquid solution of biotechnologically generated natrium-hyaluronate with a molecular weight of 1.2 million Dalton. The resulting kneadable material was highly suitable as a plastic bone-replacement material.

Example 20

A mixture of 0.3 g of porous and angular granulates of calcium-deficient hydroxylapatite (CDHA; $Ca_9(PO_4)_5$ (HPO$_4$)OH) with a specific surface of 102 sqm/g, an approximate size of 125 micrometers and a sphericity degree of S=1.8 and 0.3 g of porous and angular granulates of calcium-deficient hydroxylapatite (CDHA; Ca$_9$(PO$_4$)$_5$(HPO$_4$)OH) with a specific surface of 102 sqm/g, an approximate size of 500 micrometers and a sphericity of S=2.3 was mixed with 2.7 g of a 10% liquid solution of biotechnologically generated natrium-hyaluronate with a molecular weight of 1.2 million Dalton. The resulting kneadable material was highly suitable as a plastic bone-replacement material.

Example 21

A mixture of 0.3 g of porous and angular granulates of calciumsulfate-hemihydrate with an approximate size of 125 micrometers and a sphericity degree of S=1.8 and 0.3 g of porous and angular granulates of beta-tricalcium-phosphate (β-TCP) with an approximate grain size of 500 micrometers and a sphericity of S=2.3 was mixed with 2.7 g of a 7% liquid solution of biotechnologically generated natrium-hyaluronate with a molecular weight of 1.4 million Dalton. The resulting kneadable material was highly suitable as a plastic bone-replacement material.

What is claimed:

1. A kneadable and moldable bone-replacement material which consists of a mixture of:
   A) calcium-containing ceramic particles comprising pore size(s) from 100 to 500 micrometers;
   B) a hydrogel or a substance that can be swelled into a hydrogel having a molecular weight greater than about 300,000 Daltons, and
   wherein the ceramic particles are of fully synthetic origin; the individual ceramic particles have at least a partially cohesive, porous structure; and at least 60% of the ceramic particles have an angular shape, wherein the porosity of the ceramic particles is between 60 and 90 percent.

2. The bone-replacement material in accordance with claim 1, wherein pore size of the ceramic particles is between 340 and 450 micrometers.

3. The bone-replacement material in accordance with claim 1, wherein the bulk density of the ceramic particles is between 0.2 g/cm$^3$ and 2.0 g/cm$^3$.

4. The bone-replacement material in accordance claim 1, wherein the jarring density of the ceramic particles is between 0.5 g/cm$^3$ and 2.5 g/cm$^3$.

5. The bone-replacement material in accordance with claim 1, wherein the average diameter of the ceramic particles is between 100 and 250 micrometers.

6. The bone-replacement material in accordance with claim 1, wherein the average diameter of the ceramic particles is between 250 and 500 micrometers.

7. The bone-replacement material in accordance with claim 1, wherein the average diameter of the ceramic particles is between 0.5 and 5.6 mm.

8. The bone-replacement material in accordance with claim 1, wherein ceramic particles with an average diameter of 100 to 250 micrometers are used together with those having an average diameter of 250 to 500 micrometers and/or together with those having an average diameter of 0.5 to 5.6 mm.

9. The bone-replacement material in accordance with claim 1, wherein the ceramic particles consist of a calcium-phosphate having a molar Ca/P relationship between 1.0 and 2.0.

10. The bone-replacement material in accordance with claim 1, wherein the ceramic particles consist of a mixture of different calcium-phosphates.

11. The bone-replacement material in accordance with claim 1, wherein the ceramic particles consist of a calcium-sulfate.

12. The bone-replacement material in accordance with claim 1, wherein the ceramic particles consist of a calcium-carbonate.

13. The bone-replacement material in accordance with claim 1, wherein the ceramic particles consist of a mixture of different calcium-phosphates, calcium-sulfates and/or calcium-carbonates.

14. A kneadable and moldable bone-replacement material which consists of a mixture of:
   A) calcium-containing ceramic particles comprising pore size(s) from 100 to 500 micrometers;
   B) a hydrogel or a substance that can be swelled into a hydrogel having a molecular weight greater than about 300,000 Daltons, and
   wherein the ceramic particles are of fully synthetic origin; the individual ceramic particles have at least a partially cohesive, porous structure; at least 60% of the ceramic particles have an angular shape, wherein the porosity of the ceramic particles is between 60 and 90 percent; and
   C) metallic or semi-metallic ion shares as additives.

15. The bone-replacement material in accordance with claim 1, wherein the hydrogel or the substance which can be swollen into a hydrogel consists of fully synthetic substances.

16. The bone-replacement material in accordance with claim 1, wherein the hydrogel or the substance which can be swelled into a hydrogel consists of natural biological substances.

17. The bone-replacement material in accordance with claim 1, wherein the hydrogel or the substance which can be swollen into a hydrogel consists of a biotechnologically generated substance.

18. The bone-replacement material in accordance with claim 1, wherein the hydrogel is a liquid solution of a hyaluronate.

19. The bone-replacement material in accordance with claim 1, wherein the weight relationship A/B between the hydrated hydrogel and the calcium-containing ceramic particles is between 0.2 and 5.

* * * * *